US010258547B2

(12) United States Patent
Kasai et al.

(10) Patent No.: US 10,258,547 B2
(45) Date of Patent: Apr. 16, 2019

(54) COSMETIC FOAM COMPOSITIONS COMPRISING UV SUNSCREENS AND MINERAL FILLERS

(75) Inventors: Takehiko Kasai, Tokyo (JP); Takahiro Suzuki, Tokyo (JP)

(73) Assignee: L'OREAL, Paris (FR)

( * ) Notice: Subject to any disclaimer, the term of this patent is extended or adjusted under 35 U.S.C. 154(b) by 0 days.

(21) Appl. No.: 13/144,004

(22) PCT Filed: Jan. 29, 2009 (Under 37 CFR 1.47)

(86) PCT No.: PCT/IB2009/050368

§ 371 (c)(1), (2), (4) Date: Jan. 30, 2012

(87) PCT Pub. No.: WO2010/086695

PCT Pub. Date: Aug. 5, 2010

(65) Prior Publication Data

US 2012/0213712 A1 Aug. 23, 2012

(51) Int. Cl.

| | |
|---|---|
| ***A61K 8/02*** | (2006.01) |
| ***A61K 8/18*** | (2006.01) |
| ***A61K 9/12*** | (2006.01) |
| ***A61Q 17/04*** | (2006.01) |
| ***A61K 8/04*** | (2006.01) |
| ***A61K 8/19*** | (2006.01) |
| ***A61K 8/25*** | (2006.01) |
| ***A61K 8/40*** | (2006.01) |

(52) U.S. Cl.

CPC ................ *A61K 8/046* (2013.01); *A61K 8/19* (2013.01); *A61K 8/25* (2013.01); *A61K 8/40* (2013.01); *A61Q 17/04* (2013.01); *A61K 2800/87* (2013.01)

(58) Field of Classification Search

CPC ....... A61K 8/046; A61K 8/19; A61K 2800/87

USPC ..................................................... 424/47, 59

See application file for complete search history.

(56) References Cited

U.S. PATENT DOCUMENTS

| | | | | |
|---|---|---|---|---|
| 3,673,105 | A | 6/1972 | Curtis et al. | |
| 5,961,957 | A * | 10/1999 | McAnalley | 424/45 |
| 2004/0170582 | A1 | 9/2004 | Harivel | |
| 2004/0234559 | A1 | 11/2004 | Bleckmann et al. | |
| 2004/0241105 | A1 | 12/2004 | Riedel et al. | |
| 2005/0079142 | A1 | 4/2005 | Brunckhorst et al. | |
| 2007/0160636 | A1 * | 7/2007 | Kasai | 424/401 |

FOREIGN PATENT DOCUMENTS

| | | | |
|---|---|---|---|
| DE | 102 55 991 | A1 | 6/2004 |
| DE | 20 2005 011 885 | U1 | 8/2006 |
| EP | 1 388 338 | A1 | 2/2004 |
| EP | 1 500 385 | A1 | 1/2005 |
| EP | 1992 323 | A1 | 11/2008 |
| FR | 553 803 | | 5/1923 |
| JP | 2000-247824 | A | 9/2000 |
| JP | A-2004-519499 | | 7/2004 |
| JP | A-2005-506325 | | 3/2005 |
| WO | WO 03/088941 | A1 | 10/2003 |

OTHER PUBLICATIONS

English Translation of DE 10255991; Accessed Jan. 13, 2013 on espacenet.com.*

Socal 90A, Product Data Sheet, p. 1, Solvay Advanced Functional Minerals, 2005, Accessed May 29, 2013.*

Chemical Book webpage, http://www.chemicalbook.com/ChemicalProductProperty_US_CB5853119.aspx, accessed online Feb. 12, 2018.*

International Search Report issued in International Application No. PCT/IB2009/050368 dated Nov. 30, 2009.

Written Opinion of the International Searching Authority issued in International Application No. PCT/IB2009/050368 dated Nov. 30, 2009.

* cited by examiner

*Primary Examiner* — Kevin S Orwig

(74) *Attorney, Agent, or Firm* — Oliff PLC

(57) ABSTRACT

The present invention relates to a cosmetic composition in the foam form comprising, in a physiologically acceptable medium, at least one aqueous phase, talc and one UV sunscreen ingredient. It also relates to a cosmetic composition in the foam form comprising, in a physiologically acceptable medium, at least one aqueous phase, at least 1% by weight of at least one mineral filler relative to its total weight, and one UV sunscreen ingredient.

32 Claims, No Drawings

COSMETIC FOAM COMPOSITIONS COMPRISING UV SUNSCREENS AND MINERAL FILLERS

The present invention relates to a composition in the foam form for caring for and/or making up keratin materials.

The composition according to the invention may be, for example, a composition for making up or caring for keratinous substances, in particular the skin, lips, eyelashes, eyebrows or nails. The composition may or may not be coloured.

The make-up composition may be selected from, e.g., a foundation, a face powder, an eye shadow, a concealer, a blusher, a lipstick, a lip balm, a lip gloss, a mascara, an eyeliner and a product for making up the body or colouring the skin. It may especially be a foundation base.

The care composition may be a product for caring for the eyelashes, lips or skin of the body and face, in particular an antisun product.

It has already been proposed to introduce a gas, generally air, into cosmetic compositions to give them a light texture and the appearance of a foam. This is known as overrunning. The emulsions in the foam form thus obtained are appreciated for their lightness on application.

Cosmetic compositions of this type are generally in the form of temporary foam produced just before use.

These are either aerosol products distributed from a pressurized container, with the aid of a propellant and thus forming a foam, or compositions distributed from a container using a mechanical pump connected to a distribution head.

However, the compositions in the foam form currently available are not always entirely satisfactory, firstly in terms of quality of the foam and secondly in terms of durability of the foam. In most cases, the foam aspect generally generated at the time of distribution very rapidly degrades. More specifically, the mousse very quickly has a tendency to collapse.

Improved overrun compositions comprising at least one aqueous phase and at least one filler and having a density of less than or equal to 0.12 g/cm$^3$ have already been described in patent application FR 05 53803.

The presence of a substantial amount of mineral fillers, and more especially of talc, appears however to be prejudicial to the foam stability over time.

There still remains thus a need for compositions in the foam form comprising at least one aqueous phase and talc and exhibiting a satisfying foam stability over time.

There remains also a need for compositions in the foam form comprising at least one aqueous phase and at least 1% by weight of at least one mineral filler relative to its total weight and exhibiting a satisfying foam stability over time.

The present invention is directed towards proposing a composition in the foam form of improved density, especially in terms of stability, satisfying parts or all of these needs.

It has now been unexpectedly discovered that the use of some particular UV sunscreen ingredients was advantageous for these purposes.

It is known from US 2005/0079142 that one or more UV filter substances may be used for the foam-boosting of self-foaming, foam-like, after foaming or foamable cosmetic and dermatological preparations which comprise at least one polar oil component.

This document does not teach however that such UV sunscreen ingredients may also be useful in compositions in the foam form comprising especially a mineral filler, and in particular talc.

Thus, according to one of its aspects, the present invention relates to a cosmetic composition in the foam form comprising, in a physiologically acceptable medium, at least one aqueous phase, talc and one UV sunscreen ingredient.

According to another of its aspects, the present invention relates to a cosmetic composition in the foam form comprising, in a physiologically acceptable medium, at least one aqueous phase, at least 1% by weight of at least one mineral filler relative to its total weight, and one UV sunscreen ingredient.

The compositions in the foam form according to the present invention exhibit good stability over time, in particular in terms of homogeneity, foam stability, and appearance of the product.

The composition in the foam form according to the invention may be obtained from a base composition packaged in a product. This product may contain, besides the base composition, a propellant.

Thus, the present invention further relates to a product comprising:

a. a container defining at least one compartment;
b. a composition contained in said compartment, said composition comprising, in a physiologically acceptable medium, at least one aqueous phase, talc and one UV sunscreen ingredient;
c. a propellant to pressurize said composition inside said compartment; and
d. a dispensing head having an opening to be selectively put in fluid communication with said compartment in order to deliver said pressurized composition in the form of a foam.

The present invention also further relates to a product comprising:

a. a container defining at least one compartment;
b. a composition contained in said compartment, said composition comprising, in a physiologically acceptable medium, at least one aqueous phase, at least 1% by weight of at least one mineral filler relative to its total weight and one UV sunscreen ingredient;
c. a propellant to pressurize said composition inside said compartment; and
d. a dispensing head having an opening to be selectively put in fluid communication with said compartment in order to deliver said pressurized composition in the form of a foam.

According to yet another embodiment, the present invention relates to a kit comprising one of the product defined above and an applicator.

It also concerns a process for caring for and/or making up the body, in particular the human body, especially the face, comprising the application to the surface to be treated and/or made up of a composition in the foam form as defined above or of a composition in the foam form as delivered by one of the product defined above.

For the purposes of the invention, the term "composition(s)" means the cosmetic composition and/or the base composition.

For the purposes of the invention, a physiologically acceptable medium is a medium that is compatible with the skin, the eyes and/or the hair and is thus useful for formulating a cosmetic and/or dermatological composition.

The term "composition in (the) foam form" and the term "composition in the form of a foam" mean the same thing and are understood to mean a composition comprising a gas phase (for example air) in the form of bubbles; another equivalent term is "composition expanded in volume".

The composition in the form of a foam according to the invention is advantageous in several respects. It is easy to handle on the hand. It has a light, fresh feeling, creamy and fondant mousse texture when applied to the skin. It spreads easily and thinly on the skin and gives uniform makeup of the skin without leaving visible traces. Furthermore, after application to the skin, the makeup or the deposit obtained has a powdery, velvety finish and is comfortable to wear, without any effect of drying out or tautness; the made-up or treated skin is pleasantly soft.

The composition in the foam form preferably exhibits a light texture and is easy to withdraw and to spread over keratinous substances.

Mineral Filler

In one exemplary embodiment, the composition according to the present invention may comprise talc.

Mention may be made especially of talc sold under the tradename LUZENAC PHARMA M® by the company LUZENAC which is plate in shape and whose size is around 7.6 μm.

In another exemplary embodiment, the composition according to the present invention may comprise at least 1% by weight, for example at least 2% by weight, for example at least 3% by weight, for example at least 5% by weight of at least one mineral filler relative to its total weight.

For the purposes of the invention, the term "mineral filler" does not cover $TiO_2$ and ZnO which are both considered as pigments.

Said mineral filler may for example be selected in the group consisting of talc, silica, mica, kaolin, precipitated calcium carbonate, magnesium carbonate, magnesium hydrogen carbonate, hydroxyapatite, and mixtures thereof.

It may especially be talc, in particular as described above.

Talc may be present in an amount ranging from 1 to 25% by weight, for example from 1 to 10% by weight, preferably from 2 to 8% by weight relative to the total weight of the composition.

The composition according to the present invention may further comprise at least silica.

It may be for example surface-treated silica, such as especially silicone treated silica, such as methicone-treated silica.

Mention may be made especially of silica sold under the tradename SI-SB 700® by the company MIYOSHI which is sphere-shaped and whose size is around 5.1 μm.

Silica may be present in an amount ranging from 0.1 to 10% by weight, for example from 1 to 8% by weight, preferably from 1 to 3% by weight relative to the total weight of the composition.

The composition according to the invention may especially comprise a mineral filler, especially talc and/or silica, having a particle size ranging from 0.1 to 100 μm, for example from 1 to 10 μm, especially from 2 to 8 μm.

According to one exemplary embodiment, the composition may include talc and silica, especially in a weight ratio [talc/silica] ranging from 0.1 to 10, for example from 0.2 to 8, for example from 0.5 to 1.5, in particular of about 1.

UV Sunscreen Ingredient

The screening compositions in accordance with the invention comprise organic and/or inorganic UV sunscreen ingredients active in the UV-A and/or UV-B region which are hydrophilic and/or lipophilic.

In particular, the UV sunscreen ingredients according to the invention might have a solubility parameter ranging from 8.0 to 9.5. Said UV sunscreen ingredients have a good plasticizer function.

Advantageously, the UV sunscreen agent according to the invention might have a molecular weight ranging from 150 to 500 g/mol and contain hydrophobic sites and benzene nucleus or electron resonance group binding with polar sites.

The hydrophilic and/or lipophilic organic UV sunscreen ingredients are selected in particular from dibenzoylmethane derivatives; cinnamic derivatives; salicylic derivatives; benzophenone derivatives; β,β-diphenylacrylate derivatives; p-aminobenzoic acid (PABA) derivatives; and their mixtures.

Mention may be made, as examples of organic UV sunscreen ingredients, of those denoted below under their INCI names:

para-Aminobenzoic acid derivatives:
- PABA,
- Ethyl PABA,
- Ethyl Dihydroxypropyl PABA,
- Ethylhexyl Dimethyl PABA, marketed in particular under the trademark "Escalol 507" by ISP,
- Glyceryl PABA, Dibenzoylmethane Derivatives:
- Butyl Methoxydibenzoylmethane, marketed in particular under the trademark "Parsol 1789" by Hoffmann-LaRoche,
- Isopropyl Dibenzoylmethane, Salicylic Derivatives:
- Homosalate, marketed under the trademark "Eusolex HMS" by Rona/EM Industries,
- Ethylhexyl Salicylate, marketed under the trademark "Neo Heliopan OS" by Haarmann and Reimer,
- Dipropyleneglycol Salicylate, marketed under the trademark "Dipsal" by Scher,
- TEA Salicylate, marketed under the trademark "Neo Heliopan TS" by Haarmann and Reimer, Cinnamic Derivatives:
- Ethylhexyl Methoxycinnamate, marketed in particular under the trademark "Parsol MCX" by Hoffmann-LaRoche,
- Isopropyl Methoxycinnamate,
- Isoamyl Methoxycinnamate, marketed under the trademark "Neo Heliopan E 1000" by Haarmann and Reimer,
- Cinoxate,
- DEA Methoxycinnamate,
- Diisopropyl Methylcinnamate,
- Glyceryl Ethylhexanoate Dimethoxycinnamate, β,β-Diphenylacrylate Derivatives:
- Octocrylene, marketed in particular under the trademark "Uvinul N539" by BASF,
- Etocrylene, marketed in particular under the trademark "Uvinul N35" by BASF, Benzophenone Derivatives:
- Benzophenone-1, marketed under the trademark "Uvinul 400" by BASF,
- Benzophenone-2, marketed under the trademark "Uvinul D50" by BASF,
- Benzophenone-3 or Oxybenzone, marketed under the trademark "Uvinul M40" by BASF,
- Benzophenone-4, marketed under the trademark "Uvinul MS40" by BASF,
- Benzophenone-5,
- Benzophenone-6, marketed under the trademark "Helisorb 11" by Norquay, and their mixtures.

The preferred UV sunscreen ingredients are selected in the group consisting of cinnamic derivatives, β,β diphénylacrylates derivatives, salicylic derivatives, and their mixtures.

The preferred UV sunscreen ingredients are especially selected in the group consisting of ethylhexyl methoxycinnamate, octocrylene and ethylhexyl salicylate, and their mixtures.

Mention may be made especially of ethylhexyl methoxycinnamate sold under the tradename UVINUL MC 80® by the company BASF, of ethylhexyl salicylate sold under the tradename NEO HELIOPAN OS® by the company SYMRISE and of octocrylene sold under the tradename NEO HELIOPAN 303® by the company SYMRISE.

The composition in accordance with the invention may comprise from 0.1% to 30% by weight, for example from 0.5 to 20% by weight, for example from 1 to 15% by weight, and for example at least 1% by weight, of UV sunscreen ingredient relative to the total weight of the composition.

According to one exemplary embodiment, the composition may comprise the mineral filler and at least one UV sunscreen ingredient in a weight ratio [mineral filler/UV sunscreen ingredient] ranging from 0.20 to 10, for example from 1 to 9.5, preferably from 3 to 9.

According to another exemplary embodiment, the composition may comprise talc and at least one UV sunscreen ingredient in a weight ratio [talc/UV sunscreen ingredient] ranging from 0.1 to 10, for example from 0.5 to 8, preferably from 1 to 5.

According to yet another exemplary embodiment, the composition may comprise silica and at least one UV sunscreen ingredient in a weight ratio [silica/UV sunscreen ingredient] ranging from 0.1 to 10, for example from 0.4 to 8, preferably from 1 to 5.

Air or Inert Gas

The compositions in the foam form according to the invention are formed stably in the form of mousse using a base composition and air or an inert gas.

The air or the inert gas may represent especially from 10% to 500% and preferably from 20% to 200%, for example from 30% to 100% of the volume of the composition in the foam form.

This volume may be calculated by comparing the density of the base composition and of the in the foam form composition.

Besides air, gases that allow the composition in the foam form to be obtained are in particular inert gases, for example nitrogen, carbon dioxide, nitrogen oxides, noble gases or a mixture of the said gases. When the composition comprises an oxidation-sensitive compound, it is preferable to use an oxygen-free gas such as nitrogen or carbon dioxide.

The base composition serving to obtain the composition in the foam form has a composition similar to the composition in the foam form except for its higher density, insofar as it is free of air or of inert gas.

The amount of gas introduced into the base composition contributes towards adjusting the density of the composition in the foam form to the desired value, for example less than or equal to 0.12 g/cm$^3$.

The composition in the foam form of the invention may have for example a density of less than or equal to 0.12 g/cm$^3$, for example ranging from 0.02 to 0.11 g/cm$^3$ and preferably from 0.06 to 0.10 g/cm$^3$, this density being measured at a temperature of about 20° C. and at atmospheric pressure according to the following protocol.

Density Measurement

The test is performed on 50 ml of composition introduced into a 50 ml polished Plexiglas® goblet ($V_1$) defining a cylindrical filling space 30 mm high having a base with a diameter of 46 mm. The goblet has a bottom wall 10 mm thick and a side wall 12 mm thick.

Before measurement, the composition to be characterized and the goblet are maintained at a temperature of about 20° C. The goblet is tared and the weight value ($M_1$) is recorded. The composition in the foam form is then introduced into the goblet so as to occupy the total volume, while avoiding the formation of air bubbles during the filling of the goblet. The assembly is left to stand for 10 seconds to allow the mousse to expand fully. The top of the goblet is then skimmed before weighing ($M_2$). The density is assessed according to the convention $\rho=(M_2-M_1)/50$.

Stability Measurement

The composition in the foam form according to the invention shows satisfactory stability, which may be calculated by measuring the volume of mousse ($V_2$) remaining in the goblet after 10 minutes according to the protocol described above for the density measurement.

The ratio $V_2/V_1$ corresponds to the ratio between the volume of the composition in the foam form after 10 minutes and the volume of the composition in the foam form after 10 seconds.

The expression "satisfactory stability" applies especially to compositions in the foam form with a ratio $$\frac{V_2}{V_1}$$

of greater than 0.85 and especially greater than 0.90, for example greater than 0.95.

For a given weight of composition in the foam form, the volume of the composition in the foam form is inversely proportional to the density of the composition in the foam form. Thus, the ratio between the density of the composition in the foam form measured after 10 seconds and the density of the composition in the foam form measured after 10 minutes may be greater than 0.85 and especially greater than 0.90, for example greater than 0.95.

Within the composition in the foam form according to the invention, the air pause may advantageously have a number-average size ranging from 20 μm to 500 μm and preferably ranging from 100 μm to 300 μm.

Aqueous Phase

The composition according to the invention generally comprises an aqueous phase comprising water and optionally a hydrophilic organic solvent, for instance monoalcohols and polyols, in particular $C_2$ to $C_4$ polyols, for example ethylene glycol, diethylene glycol, butylene glycol or glycerol.

Needless to say, the solvents are chosen as a function of their compatibility with the desired mousse texture.

The composition according to the invention may be free of glycerol so as to avoid inducing a tacky feel.

The composition advantageously comprises water. The composition may especially comprise from 35% to 95% or even from 40% to 85% water, especially from 55% to 80% water, for example from 45% to 75% water, relative to its total weight.

The composition according to the invention may also comprise seawater, especially at least 1% by weight especially from 1 to 20% by weight, for example from 5 to 15% by weight of seawater relative to the total weight.

According to one embodiment, the composition of the invention may comprise at least 30% by weight, for example at least 40% by weight, for example from 40 to 95% by weight, for example from 40 to 85% by weight, for example from 45 to 80% by weight, for example from 45 to 75% by weight of water and/or water-soluble solvent(s) relative to its total weight.

Additional Fillers

The composition according to the invention may also comprise at least one additional filler, different from talc and silica.

The term "fillers" should be understood as meaning colourless or white, mineral or synthetic particles of any shape, which are insoluble in the medium of the compositions irrespective of the temperature at which the composition is manufactured.

The additional fillers may be mineral or organic of any shape, platelet-shaped, spherical or oblong, irrespective of the crystallographic form (for example lamellar, cubic, hexagonal, orthorhombic, etc.). Mention may be made of mica, kaolin, polyamide (Nylon®) powders, poly-β-alanine powders, polyethylene powders, tetrafluoroethylene polymer (Teflon®) powders, lauroyllysine, starch, boron nitride, hollow polymer microspheres such as those of polyvinylidene chloride/acrylonitrile, for instance Expancel® (Nobel Industrie), or of acrylic acid copolymers, silicone resin powders, especially silsesquioxane powders (silicone resin powders described especially in patent EP 293 795; for example Tospearls® from Toshiba), elastomeric polyorganosiloxane particles, precipitated calcium carbonate, magnesium carbonate, magnesium hydrogen carbonate, hydroxyapatite, hollow silica microspheres, glass or ceramic microcapsules, and metal soaps derived from organic carboxylic acids containing from 8 to 22 carbon atoms and preferably from 12 to 18 carbon atoms, for example zinc stearate, magnesium stearate, lithium stearate, zinc laurate or magnesium myristate; and mixtures thereof.

Advantageously, the additional fillers are chosen from low-density fillers. The term "low-density" means, for example, fillers with a density of less than 3.5 $g/cm^3$ and especially less than 3 $g/cm^3$. Without wishing to be bound to any theory, it appears that compositions comprising fillers of excessively high density form mousses of higher porosity.

The compositions may comprise low-density additional fillers in a content ranging from 0.5% to 30% by weight, preferably ranging from 1% to 15% by weight and preferentially ranging from 1% to 10% by weight relative to the total weight of the composition.

The compositions may also comprise additional fillers with a low refractive index and/or that substantially do not absorb the water and/or the oils of the composition.

A low refractive index is, for example, a refractive index of less than 1.7, for example less than 1.6. A filler that substantially does not absorb the water and/or the oils of the composition may advantageously contribute towards giving the composition a transparent appearance.

The additional fillers with a low refractive index and/or that substantially do not absorb the water and/or the oils of the composition may be present in the composition in a content ranging from 0.1% to 30% by weight, preferably ranging from 1% to 15% by weight and preferentially ranging from 1% to 10% by weight relative to the total weight of the composition.

Among the additional fillers with a refractive index of less than 1.6, which substantially do not absorb the water and the oils of the composition and which have a density of less than 3 $g/cm^3$, mention may be made, for example, of fluorophlogopite and mixtures thereof.

Whichever they may be, the additional fillers may be present in the compositions in a content ranging from 0.1% to 35% by weight, preferably ranging from 0.5% to 30% by weight and preferentially ranging from 1% to 25% by weight relative to the total weight of the composition.

Advantageously, the fillers under consideration according to the invention may be surface-treated so as to improve their dispersibility within the composition in the foam form. Such treatments form part of the knowledge of a person skilled in the art and certain fillers thus treated are also commercially available.

Needless to say, the compositions according to the invention may contain additional fillers with a high density or refractive index or that absorb the water and/or the oil of the composition, but in an amount adjusted so as to obtain a mousse having a satisfactory density, and in particular a low porosity and satisfactory transparency.

Physiologically Acceptable Medium

The composition of the invention may also contain at least one anionic surfactant.

This is preferably at least one foaming anionic surfactant chosen from sulfates, ether sulfates and salts thereof. Among the salts of sulfates and of ether sulfates, the sodium and triethanolamine salts are preferentially chosen. The foaming anionic surfactant that may thus be used is sodium lauryl ether sulfate, and especially the product sold under the name Texapon by the company Henkel.

In general, the composition of the invention contains an amount of anionic surfactant ranging from 0.5% to 50% by weight and preferably from 2% to 30% by weight relative to the total weight of the composition.

According to one embodiment the composition in accordance with the invention may comprise less than 5% by weight, preferably less than 3% by weight, for example less than 1% by weight of anionic surfactant relative to its total weight.

The composition according to the invention may also contain an emulsifier that may be chosen from any emulsifier conventionally used for O/W emulsions.

Examples of emulsifiers that may be mentioned include:

(1) nonionic surfactants with an HLB of greater than or equal to 9, such as oxyethylenated fatty acid esters of glycerol; oxyethylenated fatty acid esters of sorbitan; oxyethylenated fatty acid derivatives; fatty acid esters of a sugar and especially fatty esters of sucrose such as sucrose stearate, for instance the product sold under the name Tegosoft PSE 141G by the company Goldschmidt; alkyl polyglucoside ethers, and mixtures thereof;

(2) silicone emulsifiers such as oxyethylenated polydimethylsiloxanes (dimethicone copolyols), for instance the product sold under the name "DC2-5695" by the company Dow Corning.

The composition according to the invention may comprise, for example, from 0.5% to 50%, preferably from 2% to 15% and better still from 4% to 10% by weight of emulsifier(s) relative to the total weight of the composition.

According to one embodiment, the composition in accordance with the invention may comprise less than 5% by weight, preferably less than 3% by weight, for example less than 1% by weight of emulsifier(s) relative to its total weight.

According to one embodiment, the composition in accordance with the invention may comprise less than 5% by weight, for instance less than 2% by weight, especially less than 1% by weight, of hydrocarbon based emulsifier and/or co-emulsifier relative to its total weight.

The composition according to the invention generally comprises a solid or liquid fatty substance and especially a liquid fatty substance.

The composition according to the invention may thus comprise an oily phase comprising at least one oil that may be chosen from volatile oils and non-volatile oils, and mixtures thereof. Advantageously, the composition comprises at least one volatile oil and at least one non-volatile oil.

The composition according to the invention may comprise at least one volatile oil.

For the purposes of the invention, the term "volatile oil" means any oil that is capable of evaporating on contact with the skin, at room temperature and atmospheric pressure. The volatile oils of the invention are volatile cosmetic oils that are liquid at room temperature, with a non-zero vapour pressure at room temperature and atmospheric pressure, ranging in particular from 0.13 Pa to 40 000 Pa (0.001 to 300 mmHg) and preferably ranging from 1.3 Pa to 1300 Pa (0.01 to 10 mmHg).

The volatile oil may be chosen from volatile hydrocarbon-based oils, volatile silicone oils and volatile fluoro oils, and mixtures thereof.

The term "hydrocarbon-based oil" means an oil mainly containing hydrogen and carbon atoms and possibly oxygen, nitrogen, sulfur and/or phosphorus atoms.

The volatile hydrocarbon-based oils may be chosen from hydrocarbon-based oils containing from 8 to 16 carbon atoms, and especially branched $C_8$-$C_{16}$ alkanes, for instance $C_8$-$C_{16}$ isoalkanes of petroleum origin (also known as isoparaffins), for instance isododecane (also known as 2,2,4,4,6-pentamethyl-heptane), isodecane and isohexadecane, for example the oils sold under the trade names Isopar® and Permethyl®.

Volatile oils that may also be used include volatile silicones, for instance volatile linear or cyclic silicone oils, especially those with a viscosity ≤5 centistokes ($5\times10^{-6}$ $m^2/s$) and especially containing from 2 to 10 silicon atoms and preferably from 2 to 7 silicon atoms, these silicones optionally comprising alkyl or alkoxy groups containing from 1 to 10 carbon atoms. As volatile silicone oils that may be used in the invention, mention may be made especially of octamethyl cyclotetrasiloxane, decamethyl cyclopentasiloxane, dodecamethyl cyclo-hexasiloxane, heptamethyl hexyltrisiloxane, heptamethyloctyl trisiloxane, hexamethyl disiloxane, octamethyl trisiloxane, decamethyl tetrasiloxane and dodecamethyl pentasiloxane, and mixtures thereof.

Volatile oils that may also be used are volatile fluoro oils: mention may be made of nonafluoroethoxybutane, nonafluoromethoxybutane, decafluoropentane, tetradecafluorohexane and dodecafluoropentane, and mixtures thereof.

The composition according to the invention may comprise at least one non-volatile oil.

The term "non-volatile oil" means an oil that remains on the skin at room temperature and atmospheric pressure for at least several hours and that especially has a vapour pressure of less than 0.13 Pa (0.01 mmHg).

These non-volatile oils may be hydrocarbon-based oils especially of animal or plant origin, or silicone oils, or mixtures thereof. The term "hydrocarbon-based oil" means an oil mainly containing hydrogen and carbon atoms and possibly oxygen, nitrogen, sulfur and/or phosphorus atoms.

The non-volatile oils may be chosen especially from non-volatile hydrocarbon-based oils, which may be fluorinated, and/or non-volatile silicone oils.

Non-volatile hydrocarbon-based oils that may especially be mentioned include:

hydrocarbon-based oils of animal origin;

hydrocarbon-based oils of plant origin, such as triglycerides consisting of fatty acid esters of glycerol, the fatty acids of which may have varied chain lengths from $C_4$ to $C_{24}$, these chains possibly being linear or branched, and saturated or unsaturated; these oils are especially heptanoic or octanoic acid triglycerides, or alternatively wheatgerm oil, sunflower oil, grapeseed oil, sesame seed oil, corn oil, apricot oil, castor oil, shea oil, avocado oil, olive oil, soybean oil, sweet almond oil, palm oil, rapeseed oil, cottonseed oil, hazelnut oil, macadamia oil, jojoba oil, alfalfa oil, poppyseed oil, pumpkin oil, sesame seed oil, marrow oil, rapeseed oil, blackcurrant oil, evening primrose oil, millet oil, barley oil, quinoa oil, rye oil, safflower oil, candlenut oil, passionflower oil or musk rose oil; shea butter; or caprylic/capric acid triglycerides, for instance those sold by the company Stéarineries Dubois or those sold under the names Miglyol 810®, 812® and 818® by the company Dynamit Nobel;

synthetic ethers containing from 10 to 40 carbon atoms;

linear or branched hydrocarbons of mineral or synthetic origin, such as petroleum jelly, polydecenes, hydrogenated polyisobutene such as Parleam®, squalane and liquid paraffins, and mixtures thereof;

synthetic esters, for instance oils of formula $R_1COOR_2$ in which $R_1$ represents a linear or branched fatty acid residue containing from 1 to 40 carbon atoms and $R_2$ represents a hydrocarbon-based chain, which is especially branched, containing from 1 to 40 carbon atoms, on condition that $R_1+R_2\geq10$, for instance purcellin oil (cetostearyl octanoate), isopropyl myristate, isopropyl palmitate, $C_{12}$ to $C_{15}$ alkyl benzoates, hexyl laurate, diisopropyl adipate, isononyl isononanoate, 2-ethylhexyl palmitate, isostearyl isostearate, 2-hexyldecyl laurate, 2-octyldecyl palmitate, 2-octyldodecyl myristate, or alcohol or polyalcohol heptanoates, octanoates, decanoates or ricinoleates, for instance propylene glycol dioctanoate; hydroxylated esters, for instance isostearyl lactate, diisostearyl malate or 2-octyldodecyl lactate; polyol esters and pentaerythritol esters;

fatty alcohols that are liquid at room temperature with a branched and/or unsaturated carbon-based chain containing from 12 to 26 carbon atoms, for instance octyldodecanol, isostearyl alcohol, oleyl alcohol, 2-hexyldecanol, 2-butyloctanol or 2-undecylpentadecanol, and higher fatty acids such as oleic acid, linoleic acid or linolenic acid, and mixtures thereof.

The non-volatile silicone oils that may be used in the composition according to the invention may be non-volatile polydimethylsiloxanes (PDMS), polydimethylsiloxanes comprising alkyl or alkoxy groups, which are pendent and/or at the end of a silicone chain, these groups each contain from 2 to 24 carbon atoms, phenyl silicones, for instance phenyl trimethicones, phenyl dimethicones, phenyltrimethylsiloxydiphenylsiloxanes, diphenyl dimethicones and diphenyl-methyldiphenyltrisiloxanes, and mixtures thereof.

The composition according to the invention advantageously comprises from 1% to 40% by weight, preferably from 2% to 30% by weight and better still from 5% to 20% by weight of oily phase relative to its total weight.

The other fatty substances that may be present in the oily phase may be, for example, fatty acids, fatty alcohols such as cetyl alcohol, and waxes.

Thus, the fatty phase may also comprise compounds that are solid at room temperature (20° C.) such as waxes, these components possibly improving the stability of the composition in the foam form. These compounds are added either in molten form or in solid form to the oily phase, heated to a temperature above the melting point of the solid. These compounds may be waxes or compounds similar to waxes, for example natural renewable waxes (insect waxes, animal waxes and plant waxes), fossil waxes (petroleum wax, lignite wax, peat wax or ozokerite), synthetic waxes (Fischer-Tropsch waxes, polyethylene waxes or amide waxes), high-melting paraffins, esters, fats, long-chain carboxylic acids or long-chain alcohols of $C_{10}$ to $C_{22}$, each of these waxes having a melting or solidification point of above room temperature (20° C.).

According to one embodiment, the composition in accordance with the invention may comprise less than 5% by weight of fatty alcohols, preferably less than 3% by weight, for example less than 1% by weight, even less than 0.5% by weight relative to its total weight.

The composition according to the invention may comprise at least one dyestuff chosen especially from pigments, nacres, liposoluble dyes and water-soluble dyes, and mixtures thereof.

The term "pigments" should be understood as meaning white or coloured, mineral or organic particles of any shape, which are insoluble in the physiological medium and are intended to colour the composition.

The term "nacres" should be understood as meaning iridescent particles of any shape, especially produced by certain molluscs in their shell or else synthesized.

The term "dyes" should be understood as meaning generally organic compounds that are soluble in water or in fatty substances such as oils.

The pigments may be white or coloured, and mineral and/or organic. Among the mineral pigments that may be mentioned are titanium dioxides, optionally surface-treated, zirconium oxide and cerium oxide, and also zinc oxide, iron oxide (black, yellow or red) or chromium oxide, manganese violet, ultramarine blue, chromium hydrate and ferric blue and metal powders such as aluminium powder or copper powder.

An example that may be mentioned is micronized titanium dioxide powder surface-treated with a silica/aluminium hydroxide/alginic acid mixture, sold under the name MT-100AQ.

Among the organic pigments that may be mentioned are carbon black, pigments of D&C type and lakes based on cochineal carmine or on barium, strontium, calcium or aluminium.

The nacreous pigments may be chosen from white nacreous pigments such as mica coated with titanium or with bismuth oxychloride, coloured nacreous pigments such as titanium mica coated with iron oxides, titanium mica coated especially with ferric blue or with chromium oxide, titanium mica coated with an organic pigment of the abovementioned type, and also nacreous pigments based on bismuth oxychloride.

The liposoluble dyes are, for example, Sudan red, D&C Red No 17, D&C Green No 6, β-carotene, soybean oil, Sudan brown, D&C Yellow No 11, D&C Violet No 2, D&C Orange No 5, quinoline yellow, annatto and bromo acids.

The dyestuffs may be present in a content ranging from 0.1% to 30% by weight, preferably ranging from 0.1% to 20% by weight, preferably ranging from 0.5% to 15% by weight, preferentially ranging from 1% to 15% by weight and more preferentially ranging from 5% to 15% by weight relative to the total weight of the composition.

In a known manner, the composition of the invention may also contain adjuvants that are common in cosmetics, such as humectants, preserving agents, antioxidants, complexing agents, solvents, fragrances, bactericides, odour absorbers, vitamins, moisturizers, self-tanning compounds and anti-wrinkle active agents. The amounts of these various adjuvants are those conventionally used in the field under consideration, for example from 0.01% to 20% of the total weight of the composition. Depending on their nature, these adjuvants may be introduced into the fatty phase, into the aqueous phase and/or into lipid vesicles.

According to one embodiment, the composition may comprise more than 1% by weight, for example from 1 to 35% by weight, for example at least 5% by weight for example at least 10% by weight, for example at least 15% by weight, for example at least 20% by weight of particulate material relative to its total weight.

Needless to say, a person skilled in the art will take care to select this or of these optional additional compound(s), and/or the amount thereof, such that the advantageous properties of the composition according to the invention are not, or are not substantially, adversely affected by the envisaged addition.

The composition in the foam form according to the invention finds its application in a wide variety of treatments, especially cosmetic treatments, of the skin, the lips and the hair, including the scalp, especially for treating, protecting or caring for the skin, the lips and/or the hair, and/or for making up the skin and/or the lips. It may also be intended for treating dry skin and/or dry lips.

Thus, a subject of the invention is also the cosmetic use of the composition in the foam form as defined above for treating, protecting or caring for the skin, the lips and/or the hair, and/or for making up the skin and/or the lips, in particular for preparing a foundation or a foundation base.

A subject of the invention is also the use of a product as defined above to form a composition in the foam form serving as a base for the preparation of a makeup of foundation type.

As non-limiting illustrations of compositions in accordance with the invention, mention may be made more particularly of those combining at least talc, silica, and a UV sunscreen ingredient chosen among ethylhexyl methoxycinnamate, octocrylene and ethyl hexyl salicylate.

Said composition may further comprise calcium carbonate and micronized titanium dioxide powder surface-treated with a silica/aluminium hydroxide/alginic acid mixture.

The composition before expansion in volume can be provided in the suspension, dispersion, solution or gel form.

Preparation Process

The composition in the foam form may be obtained from a base composition in a distributor. This distributor may be an aerosol containing, besides the base composition, a propellant.

This propellant may represent less than 20% by weight of the base composition and in particular may represent from 1% to 10% by weight, for example from 2 to 8% by weight, for example at least 5% by weight of the total weight of the base composition. The propellant that may be used may be chosen from carbon dioxide, nitrogen, nitrous oxide and volatile hydrocarbons such as butane, isobutane, propane, ethane, pentane, isododecane or isohexadecane, and mixtures thereof.

It may especially be a propane/butane mixture (Liquified Petroleum Gas or LPG) in a weight ratio [propane/butane] ranging from 0.1 to 1, especially of 0.31.

The pressure of the propellant, and for example of said propane/butane mixture, in the aerosol may range from 0.20 to 0.50 MPa, for example from 0.20 to 0.40, and especially from 0.25 to 0.35 MPa.

The compositions employed in the invention can be prepared by processes for mixing, stirring or dispersing compressed gases, such as air, chlorofluorocarbon-based compounds, nitrogen, carbon dioxide, oxygen or helium, a process for mixing and stirring in the presence of a foaming agent, such as a surfactant.

In particular, the composition is prepared by mixing the ingredients with stirring, generally under hot conditions, and by then expanding in volume under the action of a gas, it being possible for the gas to be introduced during the stage of cooling the composition or after preparation of the composition, for example using a device for expanding in volume of Mondomix type, a beater of Kenwood type, a scraped-surface exchanger or a dynamic mixer (of IMT type, for example). The gas is preferably air or nitrogen.

The composition according to the invention can be packaged in a container delimiting at least one compartment which comprises the composition, the container being closed by a closure part. The container can be equipped with a means for the dispensing of the product. In particular, the container can be equipped with a pump.

The container can be a pot.

The container can be at least partly made of thermoplastic. Mention may be made, as examples of thermoplastics, of polypropylene or polyethylene. Alternatively, the container is made of nonthermoplastic material, in particular of glass or metal (or alloy).

The composition can be applied, e.g., by finger or using an applicator.

The container is preferably used in combination with an applicator comprising at least one application component configured in order to apply the composition to keratinous substances.

According to another advantageous embodiment, the applicator comprises an application nozzle.

EXAMPLES

The examples which follow are presented by way of illustration and without limitation of the invention. Unless otherwise indicated, the amounts are given as percent by weight.

Example 1

The following base compositions were prepared (the ingredients are named by their INCI name and their content is expressed in weight %).

| INCI name | 1 | 2 | 3 | 4 | 5 (comparative) |
|---|---|---|---|---|---|
| titanium dioxide (and) silica (and) aluminium hydroxide (and) alginic acid | 10.00 | 10.00 | 10.00 | 10.00 | 10.00 |
| talc | 4.79 | 4.79 | 4.79 | 4.79 | 4.79 |
| silica (and) methicone | 3.00 | 3.00 | 3.00 | 3.00 | 3.00 |
| iron oxides (and) silica | 0.14 | 0.14 | 0.14 | 0.14 | 0.14 |
| iron oxides (and) silica | 0.04 | 0.04 | 0.04 | 0.04 | 0.04 |
| iron oxides (and) silica | 0.03 | 0.03 | 0.03 | 0.03 | 0.03 |

-continued

| INCI name | 1 | 2 | 3 | 4 | 5 (comparative) |
|---|---|---|---|---|---|
| calcium carbonate | 2.00 | 2.00 | 2.00 | 2.00 | 2.00 |
| ethylhexyl methoxycinnamate | 7.50 | 5.00 | 3.00 | 1.00 | 0.00 |
| water | 54.91 | 57.41 | 59.41 | 61.41 | 62.41 |
| sea water | 10.00 | 10.00 | 10.00 | 10.00 | 10.00 |
| dipotassium grycyrrhizate | 0.20 | 0.20 | 0.20 | 0.20 | 0.20 |
| sodium hyaluronate | 0.01 | 0.01 | 0.01 | 0.01 | 0.01 |
| betaine | 1.00 | 1.00 | 1.00 | 1.00 | 1.00 |
| sodium dehydroacetate | 0.20 | 0.20 | 0.20 | 0.20 | 0.20 |
| glycerin | 2.00 | 2.00 | 2.00 | 2.00 | 2.00 |
| ethylhexyglycerin | 0.30 | 0.30 | 0.30 | 0.30 | 0.30 |
| caprylyl glycol | 0.50 | 0.50 | 0.50 | 0.50 | 0.50 |
| butylene glycol | 2.00 | 2.00 | 2.00 | 2.00 | 2.00 |
| PEG-12 dimethicone | 1.00 | 1.00 | 1.00 | 1.00 | 1.00 |
| phenoxyethanol | 0.25 | 0.25 | 0.25 | 0.25 | 0.25 |
| tocopheryl acetate | 0.01 | 0.01 | 0.01 | 0.01 | 0.01 |
| fragrance | 0.02 | 0.02 | 0.02 | 0.02 | 0.02 |
| propylene glycol (and) hexylene glycol (and) *hamamelis virginiana* (witch hazel) extract | 0.10 | 0.10 | 0.10 | 0.10 | 0.10 |

a) Procedure

1. Powder phase is mixed by powder mixer
2. Mixed powder phase is added in main kettle
3. Heated water phase (75-85° C.) is added in main kettle
4. Heated oil phase (75-85° C.) is added in main kettle
5. Homogenized in main kettle
6. After mixing, cooled by room temperature
7. Added surfactant and fragrance phase in main kettle
8. Homogenized in main kettle
9. Finish to make bulk (Filling Process)

10. Pour bulk in the aerosol package
11. Add LPG in aerosol package (5%, 0.31 MPa)

b) Density

The density of these compositions in the foam form has been measured according to the protocol described above, according to the convention $$\rho = \frac{M_2 - M_1}{50}$$

The results are presented in the following table:

| | Composition | | | | |
|---|---|---|---|---|---|
| | 1 | 2 | 3 | 4 | 5 (comparative) |
| Density (g/cm$^3$) after expanding in volume | 0.069 | 0.064 | 0.076 | 0.087 | 0.063 |

All these compositions in the foam form have a density of less than 0.12 g/cm$^3$ (even of less than 0.10 g/cm$^3$), this density being measured at a temperature of about 20° C. and at atmospheric pressure.

c) Stability

The stability of these compositions in the foam form has then been assessed according to the previously detailed protocol, via the volume ratio $$\frac{V_2}{V_1}$$

corresponding to the ratio between the volume of the composition in the foam form after 10 minutes and the volume of the composition in the foam form after 10 seconds.

The results are presented in the following table:

| Composition | 1 | 2 | 3 | 4 | 5 (comparative) |
|---|---|---|---|---|---|
| $\frac{V_2}{V_1}$ | greater than 0.95 | | | | less than 0.15 |

The compositions in the foam form further comprising a UV sunscreen ingredient in accordance with the invention exhibit a satisfactory stability over time.

Thus, only the compositions in the foam form in accordance with the instant invention exhibit, at the same time, an improved density and foam stability over time.

Example 2

The following base compositions were prepared (the ingredients are named by their INCI name and their content is expressed in weight %).

| INCI name | 6 | 7 | 8 | 9 | 10 | 11 |
|---|---|---|---|---|---|---|
| titanium dioxide (and) silica (and) aluminium hydroxide (and) alginic acid | 10.00 | 10.00 | 10.00 | 10.00 | 10.00 | 10.00 |
| talc | 3.00 | 7.79 | 1.00 | 4.79 | 7.79 | 1.00 |
| silica (and) methicone | 4.79 | 1.00 | 7.79 | 3.00 | 1.00 | 7.79 |
| iron oxides (and) silica | 0.14 | 0.14 | 0.14 | 0.14 | 0.14 | 0.14 |
| iron oxides (and) silica | 0.04 | 0.04 | 0.04 | 0.04 | 0.04 | 0.04 |
| iron oxides (and) silica | 0.03 | 0.03 | 0.03 | 0.03 | 0.03 | 0.03 |
| calcium carbonate | 2.00 | 2.00 | 2.00 | 2.00 | 2.00 | 2.00 |
| Octocrylene | 1.00 | 1.00 | 1.00 | 0 | 0 | 0 |
| ethylhexyl salicylate | 0 | 0 | 0 | 1.00 | 1.00 | 1.00 |
| water | 62.41 | 61.41 | 61.41 | 62.41 | 61.41 | 61.41 |
| sea water | 10.00 | 10.00 | 10.00 | 10.00 | 10.00 | 10.00 |
| dipotassium grycyrrhizate | 0.20 | 0.20 | 0.20 | 0.20 | 0.20 | 0.20 |
| sodium hyaluronate | 0.01 | 0.01 | 0.01 | 0.01 | 0.01 | 0.01 |
| betaine | 1.00 | 1.00 | 1.00 | 1.00 | 1.00 | 1.00 |
| sodium dehydroacetate | 0.20 | 0.20 | 0.20 | 0.20 | 0.20 | 0.20 |
| glycerin | 2.00 | 2.00 | 2.00 | 2.00 | 2.00 | 2.00 |
| ethylhexylglycerin | 0.30 | 0.30 | 0.30 | 0.30 | 0.30 | 0.30 |
| caprylyl glycol | 0.50 | 0.50 | 0.50 | 0.50 | 0.50 | 0.50 |
| butylene glycol | 2.00 | 2.00 | 2.00 | 2.00 | 2.00 | 2.00 |
| PEG-12 dimethicone | 1.00 | 1.00 | 1.00 | 1.00 | 1.00 | 1.00 |
| phenoxyethanol | 0.25 | 0.25 | 0.25 | 0.25 | 0.25 | 0.25 |
| tocopheryl acetate | 0.01 | 0.01 | 0.01 | 0.01 | 0.01 | 0.01 |
| fragrance | 0.02 | 0.02 | 0.02 | 0.02 | 0.02 | 0.02 |
| propylene glycol (and) hexylene glycol (and) *hamamelis virginiana* (witch hazel) extract | 0.10 | 0.10 | 0.10 | 0.10 | 0.10 | 0.10 |

These compositions have been prepared according to the procedure detailed in Example 1.

b) Density

The density of these compositions has been measured according to the protocol described in Example 1.

The results are presented in the following table:

| | Composition | | | | | |
|---|---|---|---|---|---|---|
| | 6 | 7 | 8 | 9 | 10 | 11 |
| Density | 0.066 | 0.065 | 0.074 | 0.066 | 0.068 | 0.072 |

c) Stability

The foam stability has been measured according to the protocol described in Example 1.

The results are presented in the following table:

| Composition | 6 | 7 | 8 | 9 | 10 | 11 |
|---|---|---|---|---|---|---|
| $\frac{V_2}{V_1}$ | greater than 0.95 | greater than 0.90 | greater than 0.95 | greater than 0.90 | greater than 0.95 | greater than 0.95 |

All the compositions in accordance with the invention exhibit a satisfactory stability over time.

The invention claimed is:

1. A cosmetic composition in a foam form comprising, in a physiologically acceptable medium:

at least one aqueous phase, at least 3% by weight of talc relative to the total weight of the composition, at least 3% by weight relative to the total weight of the composition of at least one organic UV sunscreen ingredient selected from the group consisting of ethylhexyl methoxycinnamate, octocrylene and ethylhexyl salicylate, and their mixtures, and at least 1% by weight of silica relative to the total weight of the composition;

wherein the cosmetic composition has a $V_2/V_1$ ratio of greater than 0.85, with the $V_2/V_1$ ratio corresponding to the ratio between the volume of the composition in the foam form after 10 minutes ($V_2$) and the volume of the composition in the foam form after 10 seconds ($V_1$).

2. The composition according to claim 1, comprising at least 5% by weight of talc relative to the total weight of the composition.

3. The composition according to claim 1, having a density of less than or equal to 0.12 g/cm$^3$.

4. The composition according to claim 1, comprising from 1 to 10% by weight of silica relative to the total weight of the composition.

5. The composition according to claim 1, including talc and silica in a weight ratio of talc/silica ranging from 1 to 10.

6. The composition according to claim 1, comprising from 3 to 30% by weight of UV sunscreen ingredient relative to the total weight of the composition.

7. The composition according to claim 1, comprising at least 30% by weight of water and/or water-soluble solvent(s) relative to the total weight of the composition.

8. A product comprising:

a) a container defining at least one compartment;

b) a cosmetic composition contained in said compartment, said composition comprising, in a physiologically acceptable medium, at least one aqueous phase, at least 3% by weight of talc relative to the total weight of the composition, and at least 3% by weight relative to the total weight of the composition of at least one organic UV sunscreen ingredient selected from the group consisting of ethylhexyl methoxycinnamate, octocrylene and ethylhexyl salicylate, and their mixtures, and at least 1% by weight of silica relative to the total weight of the composition;

c) a propellant to pressurize said cosmetic composition inside said compartment; and d) a dispensing head having an opening to be selectively put in fluid communication with said compartment in order to deliver said pressurized cosmetic composition in the form of a foam, wherein the cosmetic composition in the form of a foam has a $V_2/V_1$ ratio of greater than 0.85, with the $V_2/V_1$ ratio corresponding to the ratio between the volume of the composition in the foam form after 10 minutes ($V_2$) and the volume of the composition in the foam form after 10 seconds ($V_1$).

9. The product according to claim 8, wherein the propellant is selected from the group consisting of carbon dioxide, nitrogen, nitrous oxide, isododecane or isohexadecane and volatile hydrocarbons, and mixtures thereof.

10. The product according to claim 9, wherein the propellant is a propane/butane mixture in a weight ratio of propane/butane ranging from 0.1 to 1.

11. The product according to claim 8, comprising from 1% to 10% by weight of propellant relative to the total weight of the composition.

12. A kit comprising the product according to claim 8 and an applicator.

13. A process for caring for and/or making up the body, comprising the application to the surface to be treated and/or made up of a composition in the foam form as defined in claim 1.

14. A process for caring for and/or making up the body, comprising the application to the surface to be treated and/or made up of a composition in the foam form as delivered by the product according to claim 8.

15. The composition according to claim 1, comprising talc in an amount ranging from 3 to 8% by weight relative to the total weight of the composition.

16. The composition according to claim 1, wherein silica is surface-treated silica.

17. The composition according to claim 1, comprising silica in an amount ranging from 1 to 3% by weight relative to the total weight of the composition.

18. The composition according to claim 1, comprising talc and silica in a weight ratio of talc/silica ranging from 0.5 to 1.5.

19. The composition according to claim 1, comprising at least an organic UV sunscreen ingredient selected from the group consisting of octocrylene, ethylhexyl salicylate, and their mixtures.

20. The composition according to claim 1, comprising at least 5% by weight of the at least one organic UV sunscreen ingredient relative to the total weight of the composition.

21. The composition according to claim 1, wherein the organic UV sunscreen ingredient is ethylhexyl methoxycinnamate.

22. The product according to claim 8, wherein the organic UV sunscreen ingredient is ethylhexyl methoxycinnamate.

23. A kit comprising the product according to claim 22 and an applicator.

24. The composition according to claim 1, wherein the organic UV sunscreen ingredient is ethylhexyl salicylate.

25. The product according to claim 8, wherein the organic UV sunscreen ingredient is ethylhexyl salicylate.

26. A kit comprising the product according to claim 25 and an applicator.

27. The composition according to claim 1, wherein the organic UV sunscreen ingredient is octocrylene.

28. The product according to claim 8, wherein the organic UV sunscreen ingredient is octocrylene.

29. A kit comprising the product according to claim 28 and an applicator.

30. A cosmetic composition in a foam form comprising, in a physiologically acceptable medium:

at least one aqueous phase, at least 3% by weight of talc relative to the total weight of the composition, at least 1% by weight relative to the total weight of the composition of ethylhexyl methoxycinnamate, and at least 1% by weight of silica relative to the total weight of the cosmetic composition; wherein the cosmetic composition has a $V_2/V_1$ ratio of greater than 0.85, with the $V_2/V_1$ ratio corresponding to the ratio between the volume of the composition in the foam form after 10 minutes ($V_2$) and the volume of the composition in the foam form after 10 seconds ($V_1$).

31. A product comprising:

a) a container defining at least one compartment;

b) a cosmetic composition contained in said compartment, said composition comprising, in a physiologically acceptable medium, at least one aqueous phase, at least 3% by weight of talc relative to the total weight of the composition, and at least 1% by weight relative to the total weight of the composition of ethylhexyl methoxycinnamate, and at least 1% by weight of silica relative to the total weight of the composition;

c) a propellant to pressurize said cosmetic composition inside said compartment; and d) a dispensing head having an opening to be selectively put in fluid communication with said compartment in order to deliver said pressurized cosmetic composition in the form of a foam, wherein the cosmetic composition in the form of a foam has a $V_2/V_1$ ratio of greater than 0.85, with the $V_2/V_1$ ratio corresponding to the ratio between the volume of the composition in the foam form after 10 minutes ($V_2$) and the volume of the composition in the foam form after 10 seconds ($V_1$).

32. A kit comprising the product according to claim 31 and an applicator.

* * * * *